US008685919B2

(12) United States Patent
Meier et al.

(10) Patent No.: US 8,685,919 B2
(45) Date of Patent: Apr. 1, 2014

(54) GLUCAGON ANALOGUES

(75) Inventors: Eddi Meier, Vaerløse (DK); Ditte Riber, Frederiksberg (DK); Marie Skovgaard, København Ø (DK); Bjarne Due Larsen, Roskilde (DK); Jens Rosengren Daugaard, Virum (DK)

(73) Assignee: Zealand Pharma A/S, Glostrup (DK)

( * ) Notice: Subject to any disclaimer, the term of this patent is extended or adjusted under 35 U.S.C. 154(b) by 49 days.

(21) Appl. No.: 13/139,493

(22) PCT Filed: Dec. 15, 2008

(86) PCT No.: PCT/GB2008/004121
§ 371 (c)(1),
(2), (4) Date: Aug. 15, 2011

(87) PCT Pub. No.: WO2010/070251
PCT Pub. Date: Jun. 24, 2010

(65) Prior Publication Data
US 2011/0286982 A1    Nov. 24, 2011

(51) Int. Cl.
*A61K 38/00* (2006.01)

(52) U.S. Cl.
USPC .......................................................... 514/4.8

(58) Field of Classification Search
None
See application file for complete search history.

(56) References Cited

U.S. PATENT DOCUMENTS

| 7,994,122 | B2 | 8/2011 | Riber et al. |
|---|---|---|---|
| 2005/0070469 | A1 | 3/2005 | Bloom et al. |
| 2010/0099601 | A1 | 4/2010 | Weiss |
| 2010/0190701 | A1 | 7/2010 | Day et al. |
| 2011/0286981 | A1 | 11/2011 | Meier et al. |
| 2011/0293586 | A1 | 12/2011 | Meier et al. |
| 2011/0293587 | A1 | 12/2011 | Meier et al. |
| 2012/0178670 | A1 | 7/2012 | Riber et al. |

FOREIGN PATENT DOCUMENTS

| AU | 2008326324 A1 | 5/2009 |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 2025684 A1 | 2/2009 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |
| WO | WO-2004/096854 A2 | 11/2004 |
| WO | WO-2006/134340 A2 | 12/2006 |
| WO | WO-2007/024899 A2 | 3/2007 |
| WO | WO 2007/056362 * | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO 2008/101017 | 8/2008 |
| WO | WO-2008/152403 A1 | 12/2008 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/014946 A2 | 2/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2011/006497 A1 | 1/2011 |
| WO | WO-2011/088837 A1 | 7/2011 |
| WO | WO-2011/160630 A2 | 12/2011 |
| WO | WO-2011/160633 A1 | 12/2011 |
| WO | WO-2012/098462 A1 | 7/2012 |

OTHER PUBLICATIONS

Goke et al., "Exendin-4 is a high potency agonist and truncated exendin-(9-39)-amide an antagonist at the glucagon-like peptide 1-(7-36)-amide receptor of insulin-secreting beta-cells," *J. Biol. Chem.* 268(26):19650-19655, 1993.
International Search Report and Written Opinion from PCT/GB2008/004121 dated Jun. 30, 2009.
Abbrecht et al., "Erythrocyte life-span in mice acclimatized to different degrees of hypoxia," *J. Appl. Physiol.* 32:443-445, 1972.
Adelhorst et al., "Structure-activity studies of glucagon-like peptide-1," *J. Biol. Chem.* 269:6275-6278, 1994.
Altschul et al., "Local Alignment Statistics," *Methods in Enzymology* 266:460-480, 1996.
Authier et al., "Endosomal Proteolysis of Glucagon at Neutral pH generates the bioactive Degradation Product Miniglucagon-(19-29)," *Endocrinology* 144:5353-5364, 2003.
Blache et al., "Endopeptidase from Rat Liver Membranes, Which Generates Miniglucagon from Glucagon," *J. Biol. Chem.* 268:21748-21753, 1993.
Cavanaugh et al., "Isolation and Structural Characterization of Proglucagon-Derived Peptides, Pancreatic Polypeptide, and Somatostatin from the Urodele *Amphiuma Tridactylum*," *Gen. Compar. Endocrin.* 101:12-20, 1996.

(Continued)

*Primary Examiner* — Thomas Heard
(74) *Attorney, Agent, or Firm* — Clark & Elbing LLP; Kristina Bieker-Brady

(57) ABSTRACT

The invention provides materials and methods for promoting weight loss or preventing weight gain, and in the treatment of diabetes, metabolic syndrome and associated disorders. In particular, the invention provides novel glucagon analogue peptides effective in such methods. The peptides may mediate their effect by having increased selectivity for the GLP-1 receptor as compared to human glucagon.

37 Claims, 6 Drawing Sheets

(56) References Cited

OTHER PUBLICATIONS

Chan et al., "Suppression of weight gain by glucagon in obese Zucker rats," *Exp. Mol. Path.* 40:320-327, 1984.

Cohen et al., "Oxyntomodulin Suppresses Appetite and Reduces Food Intake in Humans," *Journal of Clinical Endocrinology & Metabolism* 88:4696-4701, 2003.

Dakin et al., "Oxyntomodulin Inhibits Food Intake in the Rat," *Endocrinology* 142:4244-4250, 2001.

Dakin et al., "Peripheral oxyntomodulin reduces food intake and body weight gain in rats," *Endocrinology* 145:2687-2695, 2004.

Day et al., "A new glucagon and GLP-1 co-agonist eliminates obesity in rodents," *Nat. Chem. Biol.* 5:749-757, 2009.

Delgado et al., "The uses and properties of PEG-linked proteins," *Crit. Rev. Ther. Drug. Carrier Syst.* 9:249-304, 1992.

Druce et al., "Investigation of structure-activity relationships of Oxyntomodulin (Oxm) using Oxm analogs," *Endocrinology* 150:1712-1721, 2008.

England et al., "Glucagon Carboxyl-Terminal Derivatives: Preparation, Purification and Characterization," *Biochemistry* 21:940-950, 1982.

Francis et al., "PEGylation of cytokines and other therapeutic proteins and peptides: the importance of biological optimisation of coupling techniques," *Int. J. Hematol.* 68:1-18, 1998.

Frandsen et al., "Glucagon: Structure-Function Relationships Invegstigated by Sequence Deletions," *Hoppe-Seyler's Z Physiol. Chem.* 362:665-677, 1981.

Gelfanov et al., "Discovery and structural optimization of high affinity co-agonists at the glucagon and GLP-1 receptors," *Understanding biology using peptides*, ed. Sylvie E. Blondelle, American Peptide Society, 2005, 763-764.

Gombotz et al. "Biodegradable Polymers for Protein and Peptide Drug Delivery," *Bioconjugate Chem.* 6:332-351, 1995.

Hjorth et al., "Glucagon and Glucagon-Like Peptide 1: Selective Receptor Recognition Via Distinct Peptide Epitopes," *J. Biol. Chem.* 269:30121-30124, 1994.

Hruby et al., "The design and biological activities of glucagon agonists and antagonists, and their use in examining the mechanisms of glucose action," *Curr. Med. Chem.—Imm., Endoc. & Metab. Agents* 1:199-215, 2001.

Hudecz et al., "Synthesis, Conformation, Biodistribution, and in Vitro Cytotoxicity of Daunomycin-Branched Polypeptide Conjugates," *Bioconjugate Chem* 3:49-57, 1992.

Joshi et al., "The Estimation of Glutaminyl Deamidation and Aspartyl Cleavage Rates in Glucagon," *Int. J. Pharma.* 273:213-219, 2004.

Kallenbach et al., "Role of the Peptide Bond in Protein Structure and Folding," The Amide Linkage, Chapter 18, pp. 599-622, 2000.

Knudsen et al., "Potent Derivatives of Glucagon-like Peptide-1 with Pharmacokinetic Properties Suitable for Once Daily Administration," *J. Med. Chem.* 43:1664-1669, 2000.

Madsen et al., "Structure-activity and protraction relationship of long-acting glucagon-like peptide-1 derivatives: importance of fatty acid length, polarity, and bulkiness," *J. Med. Chem* 50:6126-6132, 2007.

McKee et al., "Receptor binding and adenylate cyclase activities of glucagon analogues modified in the N-terminal region," *Biochemistry* 25:1650-1656, 1986.

NCBI Genbank Accession No. 721913A, downloaded Dec. 15, 2009.

Pan et al, "Design of a long acting peptide functioning as both a glucagon-like peptide-1 receptor agonist and a glucagon receptor antagonist," *J. Biol. Chem.* 281:12506-12515, 2006.

Parlevliet et al., "Oxyntomodulin ameliorates glucose intolerance in mice fed a high-fat diet," *Am. J. Physiol. Endocrinol. Metab.* 294:E142-E147, 2008.

Pratesi et al., "Poly-L-aspartic acid as a carrier for doxorubicin: a comparative in vivo study of free and polymer-bound drug," *Br. J. Cancer* 52:841-848, 1985.

Tsukada et al., "An anti-α-fetoprotein antibody-daunorubicin conjugate with a novel poly-L-glutamic acid derivative as intermediate drug carrier," *J. Natl. Cancer Inst.* 73:721-729, 1984.

Unson et al., "Glucagon antagonists: contribution to binding and activity of the amino-terminal sequence 1-5, position 12, and the putative α-helical segment 19-27," *J. Biol. Chem.* 264(2):789-794, 1989.

Unson et al., "Identification of an essential serine residue in glucagon: implication for an active site triad," *Proc. Natl. Acad. Sci. U.S.A.* 91:454-458, 1994.

Unson et al., "Positively charged residues at positions 12, 17, and 18 of glucagon ensure maximum biological potency," *J. Biol. Chem.* 273:10308-10312, 1998.

Zalipsky, "Functionalized poly(ethylene glycol) for preparation of biologically relevant conjugates," *Bioconjugate Chem.* 6:150-165, 1995.

Zhu et al., "The Role of Dipeptidyl Peptidase IV in the Cleavage of Glucagon Family Peptides: In Vivo Metabolism of Pituitary Adenylate Cyclase Activating Polypeptide-(1-38)," *J. Biol. Chem.* 278:22418-22423, 2003.

\* cited by examiner

\* p<0.05 compared to Vehicle

```
                           SEQUENCE LISTING

<160> NUMBER OF SEQ ID NOS: 24

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 8
<212> TYPE: PRT
<213> ORGANISM: Homo sapiens

<400> SEQUENCE: 2

Lys Arg Asn Arg Asn Asn Ile Ala
1               5

<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 4
<211> LENGTH: 29
<212> TYPE: PRT
<213> ORGANISM: Artificial sequence
<220> FEATURE:
<223> OTHER INFORMATION: Synthetic sequence ZP2669

<400> SEQUENCE: 4

His Ser Gln Gly Thr Phe Thr Ser Asp Tyr Ser Lys Tyr Leu Asp Ser
```

```
                1               5                  10                  15
Lys Ala Ala His Asp Phe Val Glu Trp Leu Leu Arg Ala
            20                  25
```

<210> SEQ ID NO 5
<211> LENGTH: 29
<212> TYPE: PRT
<213> ORGANISM: Artificial sequence
<220> FEATURE:
<223> OTHER INFORMATION: Synthetic sequence ZP2668

<400> SEQUENCE: 5

```
His Ser Gln Gly Thr Phe Thr Ser Asp Tyr Ser Lys Tyr Leu Asp Ser
1               5                  10                  15

Lys Ala Ala Arg Asp Phe Val Arg Trp Leu Lys Leu Ala
            20                  25
```

<210> SEQ ID NO 6
<211> LENGTH: 29
<212> TYPE: PRT
<213> ORGANISM: Artificial sequence
<220> FEATURE:
<223> OTHER INFORMATION: Synthetic sequence ZP2886
<220> FEATURE:
<221> NAME/KEY: SITE
<222> LOCATION: (2)..(2)
<223> OTHER INFORMATION: Xaa = D-Ser

<400> SEQUENCE: 6

```
His Xaa Gln Gly Thr Phe Thr Ser Asp Tyr Ser Lys Tyr Leu Asp Ser
1               5                  10                  15

Lys Ala Ala His Asp Phe Val Glu Trp Leu Leu Arg Ala
            20                  25
```

<210> SEQ ID NO 7
<211> LENGTH: 29
<212> TYPE: PRT
<213> ORGANISM: Artificial sequence
<220> FEATURE:
<223> OTHER INFORMATION: Synthetic sequence ZP2867
<220> FEATURE:
<221> NAME/KEY: MOD_RES
<222> LOCATION: (2)..(2)
<223> OTHER INFORMATION: Aib

<400> SEQUENCE: 7

```
His Ala Gln Gly Thr Phe Thr Ser Asp Tyr Ser Lys Tyr Leu Asp Ser
1               5                  10                  15

Lys Ala Ala His Asp Phe Val Glu Trp Leu Leu Arg Ala
            20                  25
```

<210> SEQ ID NO 8
<211> LENGTH: 29
<212> TYPE: PRT
<213> ORGANISM: Artificial sequence
<220> FEATURE:
<223> OTHER INFORMATION: Synthetic sequence L006-0171

<400> SEQUENCE: 8

```
His Ser Gln Gly Thr Phe Thr Ser Asp Tyr Ser Lys Tyr Leu Asp Ser
1               5                  10                  15

Lys Ala Ala Gln Asp Phe Val Glu Trp Leu Leu Arg Ala
            20                  25
```

<210> SEQ ID NO 9
<211> LENGTH: 29

```
<212> TYPE: PRT
<213> ORGANISM: Artificial sequence
<220> FEATURE:
<223> OTHER INFORMATION: Synthetic sequence L006-0172

<400> SEQUENCE: 9

His Ser Gln Gly Thr Phe Thr Ser Asp Tyr Ser Lys Tyr Leu Asp Ser
1               5                   10                  15

Lys Ala Ala His Asp Phe Val Gln Trp Leu Leu Arg Ala
            20                  25

<210> SEQ ID NO 10
<211> LENGTH: 29
<212> TYPE: PRT
<213> ORGANISM: Artificial sequence
<220> FEATURE:
<223> OTHER INFORMATION: Synthetic sequence L006-0176

<400> SEQUENCE: 10

His Ser Gln Gly Thr Phe Thr Ser Asp Tyr Ser Lys Tyr Leu Asp Ser
1               5                   10                  15

Lys Ala Ala His Asp Phe Val Glu Trp Leu Met Asn Thr
            20                  25

<210> SEQ ID NO 11
<211> LENGTH: 29
<212> TYPE: PRT
<213> ORGANISM: Artificial sequence
<220> FEATURE:
<223> OTHER INFORMATION: Synthetic sequence L006-0212

<400> SEQUENCE: 11

His Ser Gln Gly Thr Phe Thr Ser Asp Tyr Ser Lys Tyr Leu Asp Ser
1               5                   10                  15

Lys Ala Ala His Asp Phe Val Lys Trp Leu Leu Arg Ala
            20                  25

<210> SEQ ID NO 12
<211> LENGTH: 29
<212> TYPE: PRT
<213> ORGANISM: Artificial sequence
<220> FEATURE:
<223> OTHER INFORMATION: Synthetic sequence L006-0169

<400> SEQUENCE: 12

His Ser Gln Gly Thr Phe Thr Ser Asp Tyr Ser Lys Tyr Leu Asp Ser
1               5                   10                  15

Arg Ala Ala His Asp Phe Val Glu Trp Leu Leu Arg Ala
            20                  25

<210> SEQ ID NO 13
<211> LENGTH: 29
<212> TYPE: PRT
<213> ORGANISM: Artificial sequence
<220> FEATURE:
<223> OTHER INFORMATION: Synthetic sequence L006-0170

<400> SEQUENCE: 13

His Ser Gln Gly Thr Phe Thr Ser Asp Tyr Ser Lys Tyr Leu Asp Ser
1               5                   10                  15

Lys Arg Ala His Asp Phe Val Glu Trp Leu Leu Arg Ala
            20                  25

<210> SEQ ID NO 14
<211> LENGTH: 29
```

```
<212> TYPE: PRT
<213> ORGANISM: Artificial sequence
<220> FEATURE:
<223> OTHER INFORMATION: Synthetic sequence ZP2753

<400> SEQUENCE: 14

His Ser Gln Gly Thr Phe Thr Ser Asp Tyr Ser Lys Tyr Leu Asp Ser
1               5                   10                  15

Leu Ala Ala Gln Asp Phe Val Gln Trp Leu Leu Asn Thr
            20                  25

<210> SEQ ID NO 15
<211> LENGTH: 29
<212> TYPE: PRT
<213> ORGANISM: Artificial sequence
<220> FEATURE:
<223> OTHER INFORMATION: Synthetic sequence ZP2667

<400> SEQUENCE: 15

His Ser Gln Gly Thr Phe Thr Ser Asp Tyr Ser Lys Tyr Leu Asp Ser
1               5                   10                  15

Lys Ala Ala Gln Asp Phe Val Gln Trp Leu Met Asn Thr
            20                  25

<210> SEQ ID NO 16

<400> SEQUENCE: 16

000

<210> SEQ ID NO 17
<211> LENGTH: 29
<212> TYPE: PRT
<213> ORGANISM: Artificial sequence
<220> FEATURE:
<223> OTHER INFORMATION: Synthetic sequence ZP2872
<220> FEATURE:
<221> NAME/KEY: SITE
<222> LOCATION: (17)..(17)
<223> OTHER INFORMATION: Lys is covalently attached to isoGlu(Palmitoyl)

<400> SEQUENCE: 17

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 18
<211> LENGTH: 29
<212> TYPE: PRT
<213> ORGANISM: Artificial sequence
<220> FEATURE:
<223> OTHER INFORMATION: Synthetic sequence L006-0208

<400> SEQUENCE: 18

His Ser Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25
```

-continued

```
<210> SEQ ID NO 19
<211> LENGTH: 29
<212> TYPE: PRT
<213> ORGANISM: Artificial sequence
<220> FEATURE:
<223> OTHER INFORMATION: Synthetic sequence L006-0239

<400> SEQUENCE: 19

His Ser Gln Gly Thr Phe Thr Ser Asp Tyr Ser Lys Tyr Leu Asp Lys
1               5                   10                  15

Lys Ala Ala His Asp Phe Val Glu Trp Leu Leu Arg Ala
            20                  25

<210> SEQ ID NO 20
<211> LENGTH: 29
<212> TYPE: PRT
<213> ORGANISM: Artificial sequence
<220> FEATURE:
<223> OTHER INFORMATION: Synthetic sequence L006-0296

<400> SEQUENCE: 20

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 21
<211> LENGTH: 4
<212> TYPE: PRT
<213> ORGANISM: Artificial sequence
<220> FEATURE:
<223> OTHER INFORMATION: Synthetic sequence

<400> SEQUENCE: 21

Lys Lys Lys Lys
1

<210> SEQ ID NO 22
<211> LENGTH: 5
<212> TYPE: PRT
<213> ORGANISM: Artificial sequence
<220> FEATURE:
<223> OTHER INFORMATION: Synthetic sequence

<400> SEQUENCE: 22

Lys Lys Lys Lys Lys
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic sequence

<400> SEQUENCE: 23
```

```
Lys Lys Lys Lys Lys Lys
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic sequence

<400> SEQUENCE: 24

Lys Lys Lys Lys Lys Lys Lys
1               5
```

GLUCAGON ANALOGUES

CROSS-REFERENCE TO RELATED APPLICATIONS

This application is the U.S. national stage filing under 35 U.S.C. §371 of international application PCT/GB2008/004121, filed Dec. 15, 2008.

FIELD OF THE INVENTION

The present invention relates to glucagon analogues and their medical use, for example in the treatment of excess food intake, obesity and excess weight.

BACKGROUND OF THE INVENTION

Preproglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1). Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala (SEQ ID NO: 2) and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala) (SEQ ID NO: 3). The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia.

OXM is released into the blood in response to food ingestion and in proportion to meal calorie content. OXM has been shown to suppress appetite and inhibit food intake in humans (Cohen et al, Journal of Endocrinology and Metabolism, 88, 4696-4701, 2003; WO 2003/022304). In addition to those anorectic effects, which are similar to those of GLP-1, OXM must also affect body weight by another mechanism, since rats treated with oxyntomodulin show less body weight gain than pair-fed rats (Bloom, Endocrinology 2004, 145, 2687). Treatment of obese rodents with OXM also improves their glucose tolerance (Parlevliet et al, Am J Physiol Endocrinol Metab, 294, E142-7, 2008) and suppresses body weight gain (WO 2003/022304).

OXM activates both the glucagon receptor and the GLP-1 receptor with a two-fold higher potency for the glucagon receptor over the GLP-1 receptor, but is less potent than native glucagon and GLP-1 on their respective receptors. Glucagon is also capable of activating both receptors, though with a strong preference for the glucagon receptor over the GLP-1 receptor. GLP-1 on the other hand is not capable of activating the glucagon receptor. The mechanism of action of oxyntomodulin is not well understood. In particular, it is not known whether the effects of the hormone are mediated exclusively through the glucagon receptor and the GLP-1 receptor, or through one or more as-yet unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (WO 2006/134340; WO 2007/100535; WO 2008/101017).

Obesity, classified is a globally increasing health problem and is associated with various diseases, particularly cardiovascular disease (CVD), type 2 diabetes, obstructive sleep apnea, certain types of cancer, and osteoarthritis. As a result, obesity has been found to reduce life expectancy. According to 2005 projections by the World Health Organization there are 400 million adults (age>15) classified as obese worldwide. In the US, obesity is now believed to be the second-leading cause of preventable death after smoking.

The rise in obesity drives an increase in diabetes, and approximately 90% of people with type 2 diabetes may be classified obese. There are 246 million people worldwide with diabetes, and by 2025 it is estimated that 380 million will have diabetes. Many have additional cardiovascular risk factors including high/aberrant LDL and triglycerides and low HDL.

People with diabetes are 2 to 4 times more likely to develop cardiovascular disease than people without diabetes, making it the most common complication of diabetes. Cardiovascular disease accounts for about 50% of the mortality in people with diabetes. Young adults with diabetes have rates of coronary heart disease (CHD) 12-40 times higher than those in young adults without diabetes and together with the high incidence and prevalence of obesity and type 2 diabetes, the morbidity and mortality rates relating to these metabolic disorders underscore the medical need for efficacious treatment options Accordingly, there is a strong medical need for treating obesity and improving glucose tolerance.

SUMMARY OF THE INVENTION

In a first aspect, the invention provides a compound having the formula $R^1$-X-Z-$R^2$
wherein
$R^1$ is H, $C_{1-4}$ alkyl, acetyl, formyl, benzoyl or trifluoroacetyl;
$R^2$ is OH or $NH_2$;
X is a peptide which has the formula I:

(SEQ ID NO: 4)
His-Ser-Gln-Gly-Thr-Phe-Thr-Ser-Asp-Tyr-Ser-Lys-

Tyr-Leu-Asp-Ser-Lys-Ala-Ala-His-Asp-Phe-Val-Glu-

Trp-Leu-Leu-Arg-Ala or differs from formula I at up to 4 of the following positions whereby, if different from formula I:
the residue at position 2 is selected from: Aib, D-Ser;
the residue at position 12 is selected from: Leu, Arg, Dpu, Dpr, Orn;
the residue at position 16 is selected from: Arg, His, Lys, Glu, Asp;

the residue at position 17 is selected from: Arg, Leu, Dpu, Dpr, Orn;
the residue at position 18 is selected from: Arg, Lys, His, Ser, Tyr;
the residue at position 20 is selected from: Gln, Lys, Arg, Glu, Asp;
the residue at position 21 is Glu;
the residue at position 24 is selected from: Gln, Leu, Ala, Lys, Arg, Asp;
the residue at position 27 is selected from: Met, Cys, Lys, Arg, Glu;
the residue at position 28 is selected from: Asn, Ser, Lys, Glu, Ala, Leu, Asp; and
the residue at position 29 is selected from: Thr, Glu, Lys;
and Z is absent or a peptide sequence of 1-20 amino acid units selected from the group consisting of Ala, Leu, Ser, Thr, Tyr, Cys, Glu, Lys, Arg, Dbu, Dpr and Orn;
or a pharmaceutically acceptable salt thereof.

In certain embodiments of the first aspect, X may differ from formula I at up to 4 of the following positions whereby, if different from formula I:
the residue at position 2 is selected from: Aib, D-Ser;
the residue at position 16 is selected from: Arg, His, Lys, Glu;
the residue at position 17 is selected from: Arg, Leu;
the residue at position 18 is selected from: Arg, Lys, His, Ser, Tyr;
the residue at position 20 is selected from: Gln, Lys, Arg, Glu;
the residue at position 24 is selected from: Gln, Leu, Ala, Lys, Arg;
the residue at position 27 is selected from: Met, Cys, Lys, Arg, Glu;
the residue at position 28 is selected from: Asn, Ser, Lys, Glu, Ala, Leu; and
the residue at position 29 is selected from: Thr, Glu, Lys.

In certain embodiments of the first aspect, X may differ from formula I at up to 4 of the following positions whereby, if different from formula I:
the residue at position 2 is selected from: Aib, D-Ser;
the residue at position 16 is selected from: Arg, His, Lys, Glu, Gly;
the residue at position 24 is selected from: Gln, Leu, Ala, Lys, Arg;
the residue at position 27 is selected from: Met, Cys, Lys, Arg, Glu;
the residue at position 28 is selected from: Asn, Ser, Lys, Glu, Ala, Leu; and
the residue at position 29 is selected from: Thr, Glu, Lys.

While maintaining consistency with the definitions of the first aspect above, it may be desirable that X comprises one or more of the following sets of residues:
17-Lys, 18-Ala; 17-Leu, 18-Ala;
17-Lys, 18-Ala, 20-His;
17-Leu, 18-Ala, 20-His;
17-Lys, 18-Ala, 24-Glu;
17-Leu, 18-Ala, 24-Glu;
17-Lys, 18-Ala, 27-Leu;
17-Leu, 18-Ala, 27-Leu;
17-Lys, 18-Ala, 29-Ala;
17-Leu, 18-Ala, 29-Ala;
17-Lys, 18-Ala, 27-Leu, 29-Ala;
17-Leu, 18-Ala, 27-Leu, 29-Ala;
17-Lys, 18-Ala, 27-Leu, 28-Arg, 29-Ala;
17-Leu, 18-Ala, 27-Leu, 28-Arg, 29-Ala;
24-Glu, 28-Arg;
24-Glu, 28-Arg, 27-Leu;
24-Glu, 28-Arg, 27-Leu, 29-Ala;
27-Leu, 28-Arg, 29-Ala;
29-Ala;
20-Arg, 24-Arg, 27-Lys, 28-Leu;
17-Arg;
18-Arg;
20-Gln;
24-Gln;
27-Met, 28-Asn, 29-Thr; or
24-Lys
and combinations thereof.

For example, X may have the sequence:

```
                                        (SEQ ID NO: 5)
HSQGTFTSDYSKYLDSKAARDFVRWLKLA;

(SEQ ID NO: 12)
HSQGTFTSDYSKYLDSRAAHDFVEWLLRA;

(SEQ ID NO: 13)
HSQGTFTSDYSKYLDSKRAHDFVEWLLRA;

(SEQ ID NO: 8)
HSQGTFTSDYSKYLDSKAAQDFVEWLLRA;

(SEQ ID NO: 9)
HSQGTFTSDYSKYLDSKAAHDFVQWLLRA;

(SEQ ID NO: 10)
HSQGTFTSDYSKYLDSKAAHDFVEWLMNT;

(SEQ ID NO: 11)
HSQGTFTSDYSKYLDSKAAHDFVKWLLRA;

(SEQ ID NO: 6)
H-DSer-QGTFTSDYSKYLDSKAAHDFVEWLLRA;

(SEQ ID NO: 7)
H-Aib-QGTFTSDYSKYLDSKAAHDFVEWLLRA;

(SEQ ID NO: 18)
HSQGTFTSDYSKYLDSKAAKDFVEWLLRA;

(SEQ ID NO: 19)
HSQGTFTSDYSKYLDKKAAHDFVEWLLRA
or
                                        (SEQ ID NO: 20)
HSQGTFTSDYSKYLDSKAAQDFVEWLLRA.
```

In a second aspect, the invention provides a compound having the formula $R^1$-X-Z-$R^2$
wherein
$R^1$ is H, $C_{1-4}$ alkyl, acetyl, formyl, benzoyl or trifluoroacetyl;
$R^2$ is OH or $NH_2$;
X is a peptide which has the formula

```
                                        (SEQ ID NO: 4)
His-Ser-Gln-Gly-Thr-Phe-Thr-Ser-Asp-Tyr-Ser-Lys-

Tyr-Leu-Asp-Ser-Lys-Ala-Ala-His-Asp-Phe-Val-Glu-

Trp-Leu-Leu-Arg-Ala
``` or differs from formula I at up to 5 of the following positions whereby, if different from formula I:
the residue at position 2 is selected from: Aib, D-Ser;
the residue at position 16 is selected from: Arg, His, Lys, Glu;
the residue at position 17 is: Arg, Leu, Dpu, Dpr, Orn;
the residue at position 20 is selected from: Gln, Lys, Arg, Glu, Asp;
the residue at position 21 is Glu;
the residue at position 24 is selected from: Gln, Leu, Ala, Lys, Arg, Asp;
the residue at position 27 is selected from: Met, Cys, Lys, Arg, Glu;

the residue at position 28 is selected from: Asn, Ser, Lys, Glu, Ala, Leu, Asp; and the residue at position 29 is selected from: Thr, Glu, Lys;

and Z is absent or a peptide sequence of 1-20 amino acid units selected from the group consisting of Ala, Leu, Ser, Thr, Tyr, Cys, Glu, Lys, Arg, Dbu, Dpr and Orn;

or a pharmaceutically acceptable salt thereof.

In certain embodiments of the second aspect, X may differ from formula I at up to 4 of the following positions whereby, if different from formula I:

the residue at position 2 is selected from: Aib, D-Ser;

the residue at position 16 is selected from: Arg, His, Lys, Glu, Gly;

the residue at position 17 is selected from: Arg, Leu;

the residue at position 18 is selected from: Arg, Lys, His, Ser, Tyr;

the residue at position 20 is selected from: Gln, Lys, Arg, Glu;

the residue at position 24 is selected from: Gln, Leu, Ala, Lys, Arg;

the residue at position 27 is selected from: Met, Cys, Lys, Arg, Glu;

the residue at position 28 is selected from: Asn, Ser, Lys, Glu, Ala, Leu; and the residue at position 29 is selected from: Thr, Glu, Lys.

While maintaining consistency with the definitions of the second aspect above, it may be desirable that X comprises any of the sets of residues described above in relation to the first aspect, or one or more of the following sets of residues:

20-Gln, 24-Gln, 27-Met, 28-Asn, 29-Thr; or

17-Leu, 20-Gln, 24-Gln, 28-Asn, 29-Thr.

```
HSQGTFTSDYSKYLDSKAAQDFVQWLMNT    (SEQ ID NO: 15)
or

HSQGTFTSDYSKYLDSLAAQDFVQWLLNT.   (SEQ ID NO: 14)
```

The invention further provides a nucleic acid (which may be DNA or RNA) encoding a compound of the invention, an expression vector comprising such a nucleic acid, and a host cell containing such a nucleic acid or expression vector.

In a further aspect, the present invention provides a composition comprising a glucagon analogue peptide as defined herein, or a salt or derivative thereof, a nucleic acid encoding such a glucagon analogue peptide, an expression vector comprising such a nucleic acid, or a host cell containing such a nucleic acid or expression vector, in admixture with a carrier. In preferred embodiments, the composition is a pharmaceutically acceptable composition and the carrier is a pharmaceutically acceptable carrier. The glucagon peptide analogue may be a pharmaceutically acceptable acid addition salt of the glucagon analogue.

The compounds described find use in preventing weight gain or promoting weight loss. By "preventing" is meant inhibiting or reducing weight gain when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on glucose tolerance and circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the treatment of metabolic syndrome, insulin resistance, glucose intolerance, type-2 diabetes, hypertension, atherogenic dyslipidimia, atherosclerois, arteriosclerosis, coronary heart disease, or stroke. Their effects in these conditions may be as a result of or associated with their effect on body weight, or may be independent thereof.

Thus the invention provides use of a compound of the invention in the treatment of a condition as described above, in an individual in need thereof.

The invention also provides a compound of the invention for use in a method of medical treatment, particularly for use in a method of treatment of a condition as described above.

The invention also provides the use of a compound of the invention in the preparation of a medicament for the treatment of a condition as described above.

As already described, the invention extends to expression vectors comprising the above-described nucleic acid sequence, optionally in combination with sequences to direct its expression, and host cells containing the expression vectors. Preferably the host cells are capable of expressing and secreting the compound of the invention. In a still further aspect, the present invention provides a method of producing the compound, the method comprising culturing the host cells under conditions suitable for expressing the compound and purifying the compound thus produced.

The invention further provides a nucleic acid of the invention, an expression vector of the invention, or a host cell capable of expressing and secreting a compound of the invention, for use in a method of medical treatment. It will be understood that the nucleic acid, expression vector and host cells may be used for treatment of any of the disorders described herein which may be treated with the compounds themselves. References to a therapeutic composition comprising a compound of the invention, administration of a compound of the invention, or any therapeutic use thereof, should therefore be construed to encompass the equivalent use of a nucleic acid, expression vector or host cell of the invention except where the context demands otherwise.

DETAILED DESCRIPTION OF THE INVENTION

Figure 1:
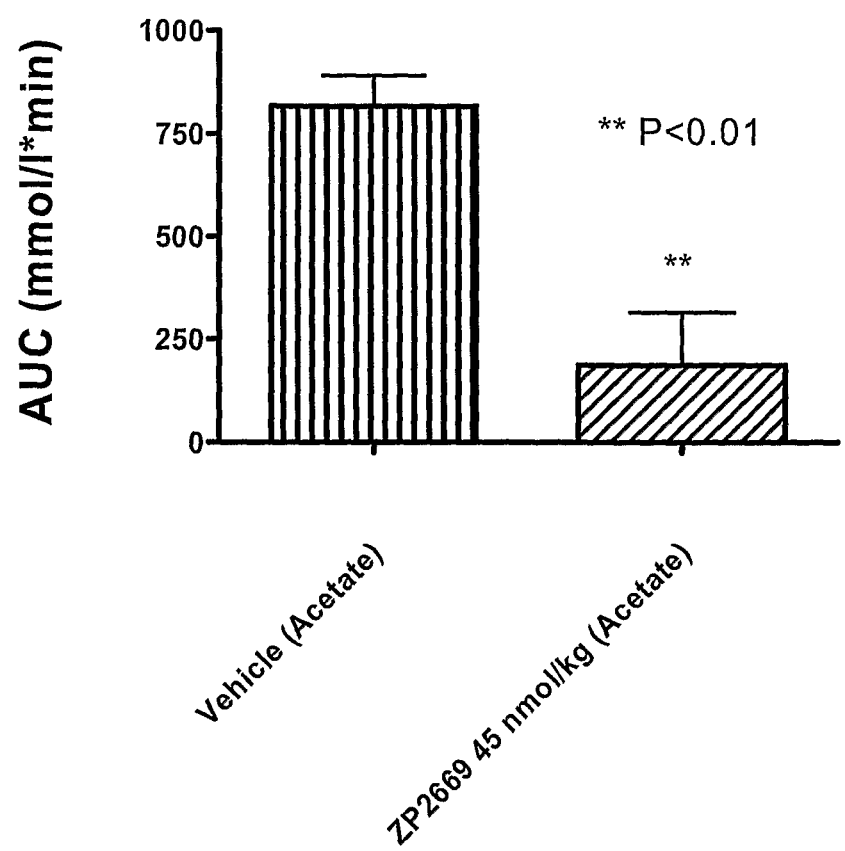
FIG. 1. Effect of ZP2669 on oral glucose tolerance in db/db mice. Db/db mice were fasted overnight and an initial blood sample (fasting blood glucose level) taken just before administration (i.p.) of vehicles or ZP2669 (45 nmol/kg). Fifteen minutes later an oral dose of glucose (1 g/kg in 5 ml/kg) was given and BG levels were measured at t=30 min, t=60 min, t=120 min and t=240 min. Difference from baseline (t=0) was calculated for each time point and $AUC_{0-240}$ min values were determined. ZP2669 significantly improved glucose tolerance in diabetic db/db mice.

Throughout this specification, the conventional one letter and three letter codes for naturally occurring amino acids are used, as well as generally accepted three letter codes for other amino acids, such as Aib (α-aminoisobutyric acid), Orn (ornithine), Dbu (2,4 diaminobutyric acid) and Dpr (2,3-diaminopropanoic acid).

The term "native glucagon" refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 1).

The terms "oxyntomodulin" and "OXM" refer to native human oxyntomodulin having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala-OH (SEQ ID NO: 3).

The invention provides compounds as defined above. For the avoidance of doubt, in the definitions provided herein, it is generally intended that the sequence of X only differs from Formula I at those positions which are stated to allow variation. Amino acids within the sequence X can be considered to be numbered consecutively from 1 to 29 in the conventional N-terminal to C-terminal direction. Reference to a "position" within X should be construed accordingly, as should reference to positions within native human glucagon and other molecules.

The compounds of the invention may carry one or more intramolecular bridge within the peptide sequence X. Each such bridge is formed between the side chains of two amino acid residues of X which are typically separated by three amino acids in the linear sequence of X (i.e. between amino acid A and amino acid A+4).

More particularly, the bridge may be formed between the side chains of residue pairs 12 and 16, 16 and 20, 17 and 21, 20 and 24, or 24 and 28. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other may be Lys or Arg. The pairings of Lys and Glu and Lys and Asp, may also be capable of reacting to form a lactam ring. Likewise, a Tyr and a Glu or a Tyr and a Asp are capable of forming a lactone ring.

In particular, the residues at positions 20 and 24 may be capable of forming an intramolecular bridge. Examples of suitable pairs of residues at these positions include:
20-Asp, 24-Lys;
20-Glu, 24-Lys;
20-Asp, 24-Arg;
20-Glu, 24-Arg;
20-Lys, 24-Asp;
20-Arg, 24-Asp;
20-Lys, 24-Glu; and
20-Arg, 24-Glu.

Without wishing to be bound by any particular theory, it is believed that such intramolecular bridges stabilise the alpha helical structure of the molecule and so increase potency and/or selectivity at the GLP-1 receptor and possibly also the glucagon receptor.

A substitution at position 12 (e.g. of Arg or Leu) may increase potency and/or selectivity at the GLP-1 receptor.

The presence of a basic amino acid (Arg, Lys or His) at position 16 may enhance the molecule's solubility and may enhance bioavailability.

The arginine residues at positions 17 and 18 of native glucagon appear to provide significant selectivity for the glucagon receptor. A number of substitutions at one or more of these positions can increase potency and/or selectivity for both the GLP-1 receptor and the glucagon receptor. Lys, or Leu at position 17 may increase potency at the glucagon receptor. Lys may be particularly effective, especially when there is a negatively charged residue (e.g. Asp) at position 21, because of the potential to form an intramolecular bridge. A hydrophobic or small hydrophilic residue (e.g. Ala or Ser) at position 18 may increase potency at both GLP-1 and glucagon receptors.

The residues at positions 27, 28 and 29 of native glucagon appear to provide significant selectivity for the glucagon receptor. Substitutions at one, two, or all three of these positions with respect to the native glucagon sequence may increase potency at and/or selectivity for the GLP-1 receptor, potentially without significant reduction of potency at the glucagon receptor. Particular examples include Leu at position 27, Arg at position 28 and Ala at position 29. 28-Arg may be particularly preferred when there is a negatively charged amino acid (e.g. Glu) at position 24 with which it can form an intramolecular bridge, which may increase its effect on potency at the GLP-1 receptor.

Substitution of the naturally-occurring Met residue at position 27 (e.g. with Leu, Lys or Glu) also reduces the potential for oxidation, so increasing the chemical stability of the compounds.

Substitution of the naturally-occurring Asn residue at position 28 (e.g. by Arg or Leu) also reduces the potential for deamidation in acidic solution, so increasing the chemical stability of the compounds.

Potency and/or selectivity at the GLP-1 receptor may also be increased by introducing residues that are likely to form an amphipathic helical structure, potentially without significant loss of potency at the glucagon receptor. This may be achieved by introduction of charged residues at one or more of positions 16, 20, 24, and 28. Thus the residues of positions 24 and 28 may all be charged, the residues at positions 20, 24, and 28 may all be charged, or the residues at positions 16, 20, 24, and 28 may all be charged. For example, the residue at position 20 may be His or Arg, particularly His. The residue at position 24 may be Glu, Asp Lys or Arg, particularly Glu. The residue at position 28 may be Arg.

Substitution of one or both of the naturally-occurring Gln residues at positions 20 and 24 also reduces the potential for deamidation in acidic solution, so increasing the chemical stability of the compounds.

The compound may comprise a C-terminal peptide sequence Z of 1-20 amino acids, for example to stabilise the conformation and/or secondary structure of the glucagon analogue peptide, and/or to make the glucagon analogue peptide more resistant to enzymatic hydrolysis, e.g. as described in WO99/46283.

When present, Z represents a peptide sequence of 1-20 amino acid residues, e.g. in the range of 1-15, more preferably in the range of 1-10 in particular in the range of 1-7 amino acid residues, e.g., 1, 2, 3, 4, 5, 6 or 7 amino acid residues, such as 6 amino acid residues. Each of the amino acid residues in the peptide sequence Z may independently be selected from Ala, Leu, Ser, Thr, Tyr, Cys, Glu, Lys, Mg, Dbu (2,4 diaminobutyric acid), Dpr (2,3-diaminopropanoic acid) and Orn (ornithine). Preferably, the amino acid residues are selected from Ser, Thr, Tyr, Cys, Glu, Lys, Arg, Dbu, Dpr and Orn, more preferably may be selected exclusively from Glu, Lys, and Cys. The above-mentioned amino acids may have either D- or L-configuration, but preferably have an L-configuration. Particularly preferred sequences Z are sequences of four, five, six or seven consecutive lysine residues (i.e. $Lys_3$, $Lys_4$ (SEQ ID NO:21), $Lys_5$ (SEQ ID NO:22), $Lys_6$ (SEQ ID NO:23) or $Lys_7$ (SEQ ID NO:24)), and particularly five or six consecutive lysine residues. Other exemplary sequences of Z are shown in WO 01/04156. Alternatively the C-terminal residue of the sequence Z may be a Cys residue. This may assist in modification (e.g. PEGylation) of the compound. In such embodiments, the sequence Z may, for example, be only one amino acid in length (i.e. Z=Cys) or may be two, three, four, five, six or even more amino acids in length. The other amino acids therefore serve as a spacer between the peptide X and the terminal Cys residue.

The peptide sequence Z has no more than 25% sequence identity with the corresponding sequence of the IP-1 portion of human OXM (which has the sequence Lys-Arg-Asn-Arg-Asn-Asn-Ile-Ala).

"Percent (%) amino acid sequence identity" of a given peptide or polypeptide sequence with respect to another polypeptide sequence (e.g. IP-1) is calculated as the percentage of amino acid residues in the given peptide sequence that are identical with corresponding amino acid residues in the corresponding sequence of that other polypeptide when the two are aligned with one another, introducing gaps for optimal alignment if necessary. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Thus, when Z is aligned optimally with the 8 amino acids of IP-1, it has no more than two amino acids which are identical with the corresponding amino acids of IP-1.

One or more of the amino acid side chains in the compound of the invention may be conjugated to a lipophilic substituent. The lipophilic substituent may be covalently bonded to an atom in the amino acid side chain, or alternatively may be conjugated to the amino acid side chain by a spacer. The amino acid may be part of the peptide X, or part of the peptide Z.

Without wishing to be bound by theory, it is thought that the lipophilic substituent binds albumin in the blood stream, thus shielding the compounds of the invention from enzymatic degradation which can enhance the half-life of the compounds. The spacer, when present, is used to provide a spacing between the compound and the lipophilic substituent.

The lipophilic substituent may be attached to the amino acid side chain or to the spacer via an ester, a sulphonyl ester, a thioester, an amide or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic substituent may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic substituent may have the formula shown below:

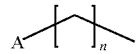

A may be, for example, an acyl group, a sulphonyl group, NH, N-alkyl, an O atom or an S atom, preferably acyl. n is an integer from 3 to 29, preferably at least 7 or at least 11, and preferably 23 or less, more preferably 19 or less.

The hydrocarbon chain may be further substituted. For example, it may be further substituted with up to three substituents selected from $NH_2$, OH and COOH. If the hydrocarbon chain is further substituted, preferably it is further substituted with only one substituent. Alternatively or additionally, the hydrocarbon chain may include a cycloalkane or heterocycloalkane, for example as shown below:

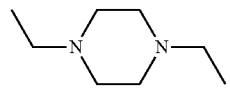

Preferably the cycloalkane or heterocycloalkane is a six-membered ring. Most preferably, it is piperidine.

Alternatively, the lipophilic substituent may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic substituent may be conjugated to the amino acid side chain by a spacer. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may have the formula:

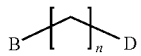

wherein B and D are each independently selected from acyl, sulphonyl, NH, N-alkyl, an O atom or an S atom, preferably from acyl and NH. Preferably, n is an integer from 1 to 10, preferably from 1 to 5. The spacer may be further substituted with one or more substituents selected from $C_{1-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic substituent as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalised side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, β-Ala, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, b-Ala and α-Gly.

The lipophilic substituent may be conjugated to any amino acid side chain in the compounds of the invention. Preferably, the amino acid side chain includes an carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys. However, any amino acid shown as Lys in the formulae provided herein may be replaced by Dbu, Dpr or Orn where a lipophilic substituent is added.

An example lipophilic substituent and spacer is shown in the formula below:

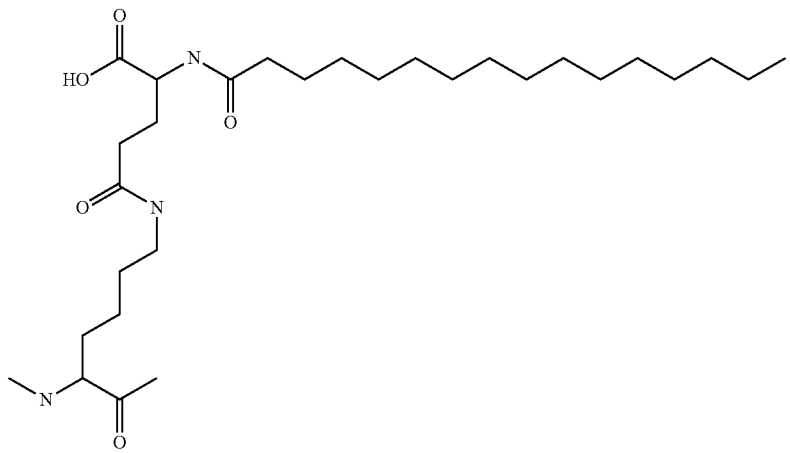 [SMILES: CCCCCCCCCCCCCCCC(=O)NC(CCC(=O)NCCCCC(NC)C(C)=O)C(=O)O]

Here, a Lys from the compound of the present invention (e.g. from X) is covalently attached to γ-Glu (the spacer) by via an amide moiety. Palmitoyl is covalently attached to the γ-Glu spacer via an amide moiety.

In a particular embodiment of the present invention, the compound comprises or consists of peptide X having the sequence:

(SEQ ID NO: 17)
HSQGTFTSDYSKYLDSK(isoGlu(Palm))AAHDFVEWLLRA

Alternatively or additionally, one or more amino acid side chains in the compound of the invention may be conjugated to a polymeric moiety, for example, in order to increase solubility and/or half-life in vivo (e.g. in plasma) and/or bioavailability. Such modification is also known to reduce clearance (e.g. renal clearance) of therapeutic proteins and peptides.

The polymeric moiety is preferably water soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), or polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J.

Natl. Cancer Inst., vol 73: 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys residues and the epsilon amino group of Lys residues, and the carboxyl groups of Asp and Glu residues may also be used.

The skilled reader will be well aware of suitable techniques which can be used to perform the coupling reaction. For example, a PEG moiety carrying a methoxy group can be coupled to a Cys thiol group by a maleimido linkage using regents commercially available from Nektar Therapeutics AL. See also WO 2008/101017, and the references cited above for details of suitable chemistry.

Peptide Synthesis

The compounds of this invention may be manufactured either by standard synthetic methods, recombinant expression systems; or any other state of the art method. Thus the glucagon analogues may be synthesized in a number of ways including for example, a method which comprises:

(a) synthesizing the peptide by means of solid phase or liquid phase methodology either stepwise or by fragment assembling and isolation and purification of the final peptide product;

(b) expressing a nucleic acid construct that encodes the peptide in a host cell and recovering the expression product from the host cell culture; or (c) effecting cell-free in vitro expression of a nucleic acid construct that encodes the peptide and recovering the expression product;

or any combination of methods of (a), (b), and (c) to obtain fragments of the peptide, subsequently ligating the fragments to obtain the peptide, and recovering the peptide.

It is preferred to synthesize the analogues of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides (2nd Edition) and the Examples herein.

For recombinant expression, the nucleic acid fragments of the invention will normally be inserted in suitable vectors to form cloning or expression vectors carrying the nucleic acid fragments of the invention; such novel vectors are also part of the invention. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

In general outline, an expression vector comprises the following features in the direction and in operable linkage: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the compound of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria (such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (such as *Saccharomyces cerevisiae*), and protozoans. Alternatively, the transformed cells may be derived from a multicellular organism, i.e. it may be fungal cell, an insect cell, a plant cell, or a mammalian cell. For the purposes of cloning and/or optimised expression it is preferred that the transformed cell is capable of replicating the nucleic acid fragment of the invention. Cells expressing the nucleic fragment are useful embodiments of the invention; they can be used for small-scale or large-scale preparation of the peptides of the invention.

When producing the peptide of the invention by means of transformed cells, it is convenient, although far from essential, that the expression product is secreted into the culture medium.

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may make use the human glucagon receptor (Glucagon-R) having primary accession number GI: 4503947 and/or the human glucagon-like peptide 1 receptor (GLP-1R) having primary accession number GI:166795283. (Where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$-[GLP-1R] lower than the $EC_{50}$-[GLP-1R] of native glucagon in a particular assay may be considered to have higher potency at the GLP-1R than glucagon.

The compounds described in this specification are typically Glu-GLP-1 dual agonists, i.e. they are capable of stimulating cAMP formation at both the glucagon receptor and the GLP-1 receptor. The stimulation of each receptor can be measured in independent assays and afterwards compared to each other.

By comparing the $EC_{50}$ value for the glucagon receptor ($EC_{50}$ [Glucagon-R]) with the $EC_{50}$ value for the GLP-1 receptor, ($EC_{50}$ [GLP-1R]) for a given compound the relative glucagon selectivity (%) of that compound can be found:

Relative Glucagon-R selectivity[Compound]=(1/$EC_{50}$ [Glucagon-R])×100/((1/$EC_{50}$[Glucagon-R]+1/$EC_{50}$[GLP-1R])

The relative GLP-1R selectivity can likewise be found:

Relative GLP-1R selectivity[Compound]=(1/$EC_{50}$ [GLP-1R])×100/((1/$EC_{50}$[Glucagon-R]+1/$EC_{50}$ [GLP-1R])

A compound's relative selectivity allows its effect on the GLP-1 or glucagon receptor to be compared directly to its effect on the other receptor. For example, the higher a compound's relative GLP-1 selectivity is, the more effective that compound is on the GLP-1 receptor as compared to the glucagon receptor.

Using the assays described below, we have found the relative GLP-1 selectivity for human glucagon to be approximately 5%.

The compounds of the invention have a higher relative GLP-1R selectivity than human glucagon. Thus, for a particular level of glucagon-R agonist activity, the compound will display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$-[GLP-1-R] than glucagon while maintaining an $EC_{50}$ [Glucagon-R] that is less than 10-fold higher than that of human glucagon, less than 5-fold higher than that of human glucagon, or less than 2-fold higher than that of human glucagon.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1 selectivity of the compounds may be between 5% and 95%. For example, the compounds may have a relative selectivity of 5-20%, 10-30%, 20-50%, 30-70%, or 50-80%; or of 30-50%, 40-60,%, 50-70% or 75-95%.

Therapeutic Uses

The compounds of the invention may provide an attractive treatment option for obesity and metabolic diseases including type 2 diabetes.

Diabetes mellitus, often referred to simply as diabetes, is a syndrome of disordered metabolism, usually due to a combination of hereditary and environmental causes, resulting in abnormally high blood sugar levels (hyperglycemia).

Blood glucose levels are controlled by the hormone insulin made in the beta cells of the pancreas. Diabetes develops due to destruction of insulin producing pancreatic beta-cells (in type 1 diabetes) or resistance to the effects of insulin (in gestational diabetes) followed by beta cell loss (in type 2 diabetes). Both types of diabetes lead to hyperglycemia, which largely causes the acute signs of diabetes: excessive urine production, resulting compensatory thirst and increased fluid intake, blurred vision, unexplained weight loss, lethargy, and changes in energy metabolism.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with the metabolic syndrome are at increased risk of type 2 diabetes as well as coronary heart disease and other diseases related to other manifestations of arteriosclerosis (e.g., stroke and peripheral vascular disease). The dominant underlying risk factors for this syndrome appear to be abdominal obesity and insulin resistance and glucose intolerance, prothrombotic state (e.g. high fibrinogen or plasminogen activator inhibitor-1 in the blood), and proinflammatory state (e.g., elevated C-reactive protein in the blood).

Without wishing to be bound by any particular theory, it is believed that the compounds of the invention act as GluGLP-1 dual agonists. The dual agonist combines the effect of glucagon on fat metabolism with the effects of GLP-1 on blood glucose levels and food intake. They might therefore act in a synergistic fashion to accelerate elimination of excessive fat deposition, induce sustainable weight loss, and directly decrease morbid glucose levels to normal levels, without the risk of hypoglycemia, which is associated with concomitant use of GLP-1 agonists and sulphonylurea.

The synergetic effect of dual GluGLP-1 agonists may also result in reduction of cardiovascular risk factors such as high cholesterol and LDL, as well as an improvement in glucose tolerance, which may be entirely independent of their effect on body weight.

The compounds of the present invention can therefore be used as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of metabolic syndrome, insulin resistance, glucose intolerance, type 2 diabetes, hypertension, atherogenic dyslipidimia, atherosclerois, arteriosclerosis, coronary heart disease and stroke. These are all conditions which can be associated with obesity. However, the effects of the compounds of the invention on these conditions may be mediated in whole or in part via an effect on body weight, or may be independent thereof.

Pharmaceutical Compositions

The compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms: It may be provided in single dose injectable form, for example in the form of a pen. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Combination Therapy

The compound of the invention may be administered as part of a combination therapy with an agent for treatment of diabetes, obesity or hypertension.

In such cases, the two active agents may be given together or separately, and as part of the same pharmaceutical formulation or as separate formulations.

Thus the compound of the invention (or the salt thereof) can be used in combination with an anti-diabetic agent including but not limited to metformin, a sulfonylurea, a glinide, a DPP-IV inhibitor, a glitazone, or insulin. In a preferred embodiment the compound or salt thereof is used in combination with insulin, DPP-IV inhibitor, sulfonylurea or metformin, particularly sulfonylurea or metformin, for achieving adequate glycemic control. In an even more preferred embodiment the compound or salt thereof is used in combination with insulin or an insulin analogue for achieving adequate glycemic control. Examples of insulin analogues include but are not limited to Lantus, Novorapid, Humalog, Novomix, and Actraphane HM The compound or salt thereof can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

The analogue compound or salt thereof can be used in combination with an anti-hypertension agent including but not limited to an angiotensin-converting enzyme inhibitor, angiotensin II receptor blocker, diuretics, beta-blocker, or calcium channel blocker.

Methods

General Synthesis of Glucagon Analogues

Solid phase peptide synthesis was performed as SPPS on a microwave assisted synthesizer using standard Fmoc strategy in NMP on a polystyrene resin (TentaGel S Ram). HATU was used as coupling reagent together with DIPEA as base. Piperidine (20% in NMP) was used for deprotection. Pseudoprolines: Fmoc-Phe-Thr(.Psi. Me, Me pro)-OH and Fmoc-Asp-Ser(.Psi., Me, Me pro)-OH (purchased from NovaBiochem) were used where applicable.

Cleavage:

The crude peptide was cleaved from the resin by treatment with 95/2.5/2.5% (v/v) TFA/TIS/water at r.t. for 2 h. For peptides with a methionine in the sequence a mixture of 95/5% (v/v) TFA/EDT was used. Most of the TFA was removed at reduced pressure and the crude peptide was precipitated and washed with diethylether and allowed to dry to constant weight at ambient temperature.

HPLC Purification of the Crude Peptide

The crude peptides were purified by standard reverse phase HPLC on a PerSeptive Biosystems VISION Workstation. VISION 3.0 software was used for instrument control and data acquisition. The peptides were analysed using MS and purified to greater than 90% as determined by HPLC.

General Synthesis of Acylated Glucagon Analogues

The peptide backbone is synthesized as described above for the general synthesis of glucagon analogues, with the exception that it is acylated on the side chain of a lysine residue with the peptide still attached to the resin and fully protected on the side chain groups, except the epsilon-amine on the lysine to be acylated. The lysine to be acylated is incorporated with the use of Fmoc-Lys(ivDde)-OH. The N-terminal of the peptide is protected with a Boc group using $Boc_2O$ in NMP. While the peptide is still attached to the resin, the ivDde protecting group is selectively cleaved using 2% hydrazine hydrate in NMP. The unprotected lysine side chain is then first coupled with a spacer amino acid like Fmoc-Glu-OtBu, which is deprotected with piperidine and acylated with a fatty acid using standard peptide coupling methodology as described above. Alternatively, the histidine at the N-terminal could be incorporated from the beginning as Boc-His(Boc)-OH. Cleavage from the resin and purification are performed as described above Analysis of Peptide Stability The glucagon analogues were incubated as solid compounds at 40° C. and dissolved as solutions in 0.1M aqueous HCl (2 mg/ml). The solutions were incubated at 40° The remaining intact glucagon analogs were measured at RP-HPLC by integration of the UV signal at 220 nM The percentage remaining is a measure for the relative stability.

The solid and solutions of glucagon compounds were prior to analysis diluted in HPLC solvent to a concentration of 0.2 mg/mL and analyzed at appropriate time points.

TABLE 1

Analytical HPLC set-up.

| Column | Gemini C18 150 × 3 mm |
| --- | --- |
| Gradient (time; % B) | (0-3 min; 18% B) (3-22 min; 45% B) (22-23 min; 95% B) (23-24 min; 18% B) (24-30 min; 18% B) |
| Solvent A | 0.1% TFA in 1% MeCN:MQW |
| Solvent B | 0.085% TFA in MeCN |
| Flow | 0.300 mL/min |
| Injection Volume | 35 μL |
| Column Temp. | 30° C. |
| UV detection | 220 nm |

Generation of Cell Lines Expressing Human Glucagon- and GLP-1Receptors

The cDNA encoding either the human glucagon receptor (Glucagon-R) (primary accession number P47871) or the human glucagon-like peptide 1 receptor (GLP-1R) (primary accession number P43220) were cloned from the cDNA clones BC104854 (MGC:132514/IMAGE:8143857) or BC112126 (MGC:138331/IMAGE:8327594), respectively. The DNA encoding the Glucagon-R or the GLP-1-R was amplified by PCR using primers encoding terminal restriction sites for subcloning. The 5'-end primers additionally encoded a near Kozak consensus sequence to ensure efficient translation. The fidelity of the DNA encoding the Glucagon-R and the GLP-1-R was confirmed by DNA sequencing. The PCR products encoding the Glucagon-R or the GLP-1-R were subcloned into a mammalian expression vector containing a neomycin (G418) resistance marker.

The mammalian expression vectors encoding the Glucagon-R or the GLP-1-R were transfected into HEK293 cells by a standard calcium phosphate transfection method. 48 hr after transfection cells were seeded for limited dilution cloning and selected with 1 mg/ml G418 in the culture medium. Three weeks later 12 surviving colonies of Glucagon-R and GLP-1-R expressing cells were picked, propagated and tested in the Glucagon-R and GLP-1-R efficacy assays as described below. One Glucagon-R expressing clone and one GLP-1-R expressing clone were chosen for compound profiling.

Glucagon Receptor and GLP-1-Receptor Efficacy Assays

HEK293 cells expressing the human Glucagon-R, or human GLP-1-R were seeded at 40,000 cells per well in 96-well microtiter plates coated with 0.01% poly-L-lysine and grown for 1 day in culture in 100 μl growth medium. On the day of analysis, growth medium was removed and the cells washed once with 200 μl Tyrode buffer. Cells were incubated in 100 μl Tyrode buffer containing increasing concentrations of test peptides, 100 μM IBMX, and 6 mM glucose for 15 min at 37° C. The reaction was stopped by addition of 25 μl 0.5 M HCl and incubated on ice for 60 min. The cAMP content was estimated using the FlashPlate® cAMP kit from Perkin-Elmer. $EC_{50}$ and relative efficacies compared to reference compounds (glucagon and GLP-1) were estimated by computer aided curve fitting.

Lipolysis in Primary Rat Adipocytes

The effect of glucagon analogues on lipolysis was assessed in primary cultures of rat adipocytes. Adipocytes were isolated from epididymal fat dissected from normal young adult Sprague-Dawley rats. The fat lumps were minced, incubated and shaken (220 rpm) with collagenase (1 mg/ml) in Krebs-Ringer buffer containing 4% BSA (KRB-BSA) for 60 minutes at 37° C. The suspension was filtered through a nylon filter (160 μm pore size) and the filtrate centrifuged at 200×g for 3 min. The subjacent medium beneath the upper floating layer of adipocytes was removed with a Pasteur-pipette. The adipocytes were washed 3 times in KRB-BSA buffer by re-suspension and centrifugation. The adipocytes were re-suspended in KRB-BSA, mixed, incubated in and shaken with test compounds in 96-deep well plates (50,000 cells/well) in a total volume of 1 ml at 37° C. for 60 min. The plates were placed on ice for at least 10 min after incubation followed by centrifugation at 200×g for 3 min. 300 μl of the buffer beneath the adipocyte layer were collected in a 96-deep well plate. This process was repeated two more times and the 3 extracts collected from each culture pooled together. The glycerol formed by the lipolysis in the adipocyte cultures was measured by adding free glycerol reagent (200 μl) to aliquots (25 μl) of adipocyte extract, incubate at room temperature for 15 min and measure the absorbance at 540 nm.

Oral Glucose Tolerance Test (OGTT) in db/db Mice

Db/db mice were fasted overnight and an initial blood sample (fasting blood glucose level) taken just before administration (i.p.) of vehicle (Acetate buffer, 20 mM acetic acid, 250 mM mannitol, pH 5.0) or the test compound ZP2669 (SEQ ID NO: 4) (45 nmol/kg in acetate buffer). The animals were kept fasted during the experiment to prevent confounding food intake. Fifteen minutes later an oral dose of glucose (1 g/kg in 5 ml/kg) was given and BG levels were measured at t=30 min, t=60 min, t=120 min and t=240 min.

Difference from baseline (t=0) was calculated for each time point and $AUC_{0-240\ min}$ values were determined. Statistical analyses of AUC values by one-way ANOVA and Dunnetts post-hoc analyses were performed with GraphPad Prism version 4. Differences were considered significant at the $p<0.05$ level.

Food Intake in Normal Mice

One week before study C57Bl/6 mice (8 weeks) (N=9-12 animals in each group) were conditioned to treatment by daily injections (s.c.) of 0.2 ml vehicle and acclimatized to handling by weighing them twice a week. Mice were stratified one day before start of experiment into groups with similar body weight (BW). Groups of stratified mice were fasted overnight treated (10 μl test solution/g BW, s.c.) with $PYY_{3-36}$ (30 nmol/kg)(internal positive control), glucagon (500 nmol/kg) and ZP2669 (SEQ ID NO: 4) (500 nmol/kg) or vehicle. After one hour pre-weighed food was introduced to the mice and food intake measured by weighing the remaining food after one hour and expressed relative to body weight (mg food/g BW). Statistical analyses of food intake data by one-way ANOVA and Dunnetts post-hoc analyses were performed with GraphPad Prism version 4. Differences were considered significant at the p<0.05 level.

Effects of 28 Day Treatment of Diet Induced Obese (DIO) Mice with ZP2669 (SEQ ID NO: 4) Agonist on Body Weight Gain and Plasma Cholesterols Four weeks before drug treatments, C57Bl/6 male mice (7 weeks)) (N=10-12 animals in each group) were put on high fat diet (HFD) and their day-night cycle reversed with lights On/Off at 2000/0800 hour. Experimental animals were conditioned to treatment by daily injections (s.c.) of 0.1 ml vehicle and acclimatized to handling by weighing them twice a week one week before start of drug administrations. The day before start of experiment, mice were stratified into groups with similar body weight (BW) and the next day groups of stratified mice were treated (b.i.d.; s.c.) with ZP2669 (SEQ ID NO: 4) (500 nmol/kg) or vehicle (Acetate-buffer). ZP2669 (SEQ ID NO: 4) was given in isotonic acetate buffer (pH 4.8; 2.5 μl/g BW). A non-obese control group maintained on regular chow was treated with vehicle in the same treatment regime as the DIO groups. Body weights were recorded daily and used to administer the body weight-corrected doses of peptide throughout the study. Animals were fasted overnight before sacrifice. An eye blood sample (0.6 ml EDTA) was obtained the following morning immediately before cervical dislocation. Blood plasma samples were stored at −80° C. until analyzed for cholesterol, HDL and LDL using commercially available kits. Body weight gains throughout the treatment period were calculated for each animal by subtracting its weight at the initiation of treatment.

The effects of treatment on body weight gain and cholesterols were assessed by 2-way ANOVA with repeated measures and Bonferoni post-hoc analyses, using GraphPad Prism version 4. Differences were considered significant at the p<0.05 level.

Results

Example 1

Peptide Stability

TABLE 2

Results for recovery measured by RP-HPLC after stress.

| ZP Compound | Recovery (%) Solid peptide | Recovery (%) 0.1M HCl |
|---|---|---|
| Glucagon | 91 | 15 |
| 2669 | 98 | 58 |

The results of incubation in HCl stress solutions are shown in table 2. Both the analogue and glucagon were stable over 5 weeks at 40° C. with a recovery of over 90% purity. However, the results of the acidic degradation of the compounds shows that the glucagon analogue is almost four times more stabile than native glucagon.

Example 2

Efficacy on Glucagon and GLP-1 Receptors

TABLE 3

$EC_{50}$ values of glucagons analogues at Glucagon and GLP-1 receptors

|  |  | GLP-1R $EC_{50}$ (nM) | GLUR. $EC_{50}$ (nM) |
|---|---|---|---|
| Glucagon |  | 20 | 0.10 |
| OXM |  | 1.0 | 0.50 |
| Exendin-4 |  | 0.02 | >1,000. |
| ZP2669 (SEQ ID NO: 4) | H-HSQGTFTSDYSKYLDSKAAHDFVEWLLRA-NH2 | 0.05 | 0.05 |
| ZP2668 (SEQ ID NO: 5) | H-HSQGTFTSDYSKYLDSKAARDFVRWLKLA-NH2 | 0.08 | 0.80 |
| ZP2866 (SEQ ID NO: 6) | H-H-DSer-QGTFTSDYSKYLDSKAAHDFVEWLLRA-NH2 | 0.09 | 0.11 |
| ZP2867 (SEQ ID NO: 7) | H-H-Aib-QGTFTSDYSKYLDSKAAHDFVEWLLRA-NH2 | 0.08 | 0.06 |
| L006-0171 (SEQ ID NO: 8)* | H-HSQGTFTSDYSKYLDSKAAQDFVEWLLRA-NH2 | 0.37 | 0.78 |

TABLE 3-continued

EC$_{50}$ values of glucagons analogues at Glucagon and GLP-1 receptors

| | | GLP-1R EC$_{50}$ (nM) | GLUR. EC$_{50}$ (nM) |
|---|---|---|---|
| L006-0172 (SEQ ID NO: 9)* | H-HSQGTFTSDYSKYLDSKAAHDFVQWLLRA-NH2 | 021 | 0.37 |
| L006-0176 (SEQ ID NO: 10)* | H-HSQGTFTSDYSKYLDSKAAHDFVEWLMNT-NH2 | 0.44 | 0.57 |
| L006-0212 (SEQ ID NO: 11)* | H-HSQGTFTSDYSKYLDSKAAHDFVKWLLRA-NH2 | 0.76 | 1.23 |
| L006-0169 (SEQ ID NO: 12)* | H-HSQGTFTSDYSKYLDSRAAHDFVEWLLRA-NH2 | 0.99 | 152 |
| L006-0170 (SEQ ID NO: 13)* | H-HSQGTFTSDYSKYLDSKRAHDFVEWLLRA-NH2 | 0.50 | 0.79 |
| ZP2753 (SEQ ID NO: 14) | H-HSQGTFTSDYSKYLDSLAAQDFVQWLLNT-NH2 | 0.04 | 0.08 |
| ZP2667 (SEQ ID NO: 15) | H-HSQGTFTSDYSKYLDSKAAQDFVQWLMNT-NH2 | 0.02 | 0.07 |
| ZP2872 (SEQ ID NO: 17) | H-HSQGTFTSDYSKYLDSK(isoGlu(Palm))AAHDFVEWLLRA-NH2 | 0.103 | 0.085 |
| L006-0208 (SEQ ID NO: 18)* | H-HSQGTFTSDYSKYLDSKAAKDFVEWLLRA-NH2 | 0.57 | 0.55 |
| L006-0239 (SEQ ID NO: 19)* | H-HSQGTFTSDYSKYLDKKAAHDFVEWLLRA-NH2 | 0.98 | 1.05 |
| L006-0296 (SEQ ID NO: 20)* | H-HSQGTFTSDYSKYLDSKAAHDFVEWLLRA-OH | 0.14 | 0.12 |

Figure 6:
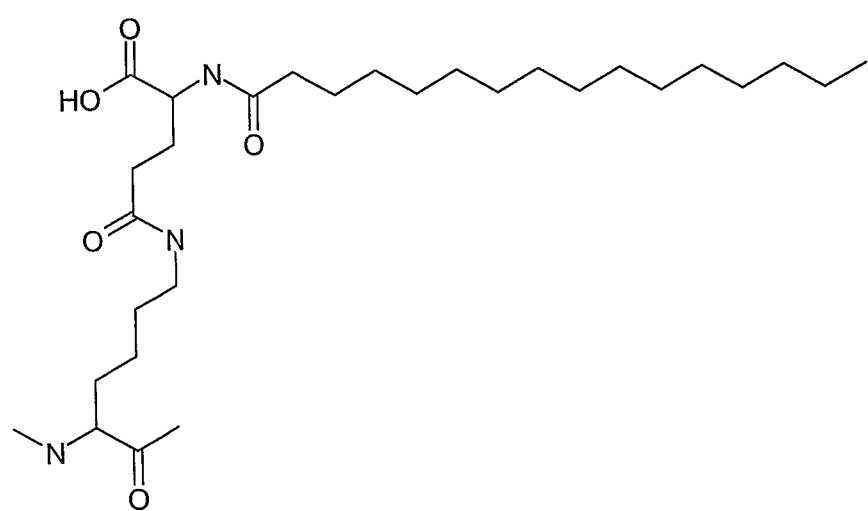
FIG. 6: The chemical modification of 17-Lys in compound ZP2872.

The compounds marked "*" are crude peptides with purity of less than 90%. The EC50 is corrected to a purity of 50%. IsoGlu(Palm) conjugated to a lysine residue is illustrated in FIG. 6.

Example 3

Lipolysis Assay

TABLE 4

Stimulation of lipolysis in primary rat adipocyte cultures (for details see Methods).

| Compound | EC50 (nM) |
|---|---|
| Exendin-4 | No effect |
| Glucagon | 6 |
| OXM | 180 |
| ZP2669 (SEQ ID NO: 4) | 4.6 |
| ZP2668 (SEQ ID NO: 5) | 101 |
| ZP2667 (SEQ ID NO: 15) | 0.75 |

The GLP-1 agonist, exendin-4 had no effect on lipolysis in primary adipocyte cultures in contrast to glucagon and OXM. ZP2667 was 8 times as potent as glucagon and 240 times as potent as OXM, while ZP2669 (SEQ ID NO: 4) was equipotent with glucagon and 40 times as potent as OXM. The potency of ZP2668 (SEQ ID NO: 5) was in the same order of magnitude as OXM. The finding that 4 weeks treatment of DIO mice with ZP2669 (SEQ ID NO: 4) significantly decreased fat deposition concurs with the effect observed (Table 4) on lipid metabolism in primary adipocyte cultures.

Example 4

Effect on Oral Glucose Tolerance in db/db Mice

ZP2669 (SEQ ID NO: 4) significantly (P<0.01) improved glucose tolerance measured during an OGTT in diabetic db/db mice (FIG. 1). ZP2669 (SEQ ID NO: 4) improved glucose tolerance by 77.1% at 45 nmol/kg.

Example 5

Effect on Food Intake in Mice

Figure 2:
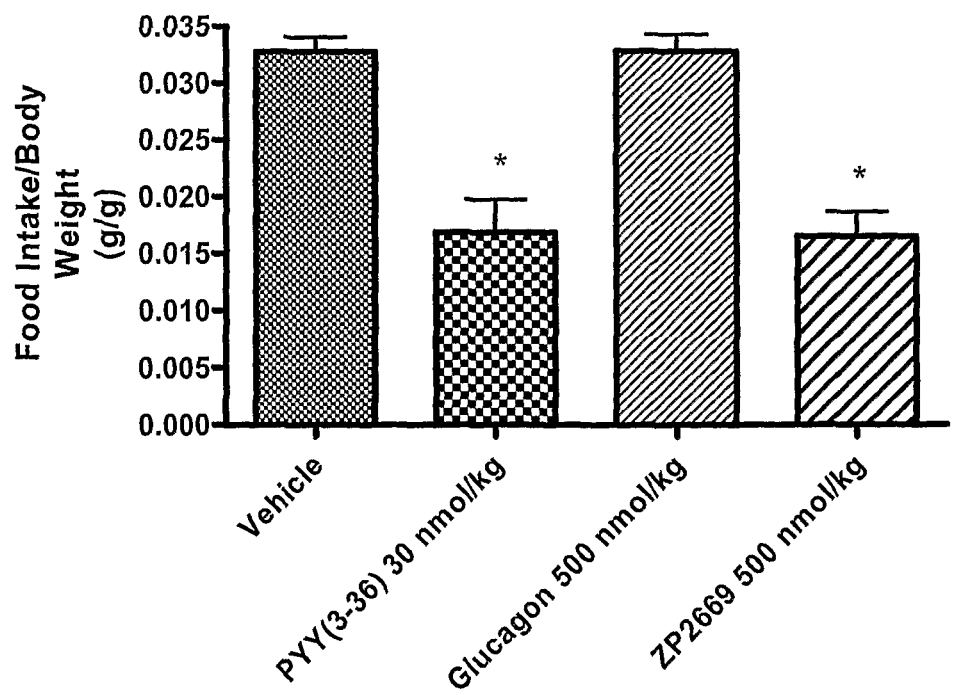
FIG. 2. Effect of ZP2669 on food intake in mice. Groups of stratified mice stratified after body weight were fasted overnight and treated with $PYY_{3-36}$ (30 nmol/kg) (internal positive control), glucagon (500 nmol/kg), ZP2669 (500 nmol/kg) or vehicle. After one hour pre-weighed food was introduced to the mice and food intake measured by weighing the remaining food after one hour and expressed relative to body weight (mg food/g BW). PYY(3-36) showed an anorectic effect as expected from previous findings. ZP2669 (500 nmol/kg) significantly decreased food intake during the first hour following injection of peptide. Glucagon had no effect on food intake.

The vehicle treated animals ate 0.033±0.001 g food/g body weight during the first hour (FIG. 2). PYY(3-36) showed an anorectic effect as expected from previous findings. ZP2669 (SEQ ID NO: 4) (500 nmol/kg) significantly (P<0.05) decreased food intake during the first hour following injection of peptide (FIG. 2). Glucagon had no effect on food intake.

Example 6

Figure 3:
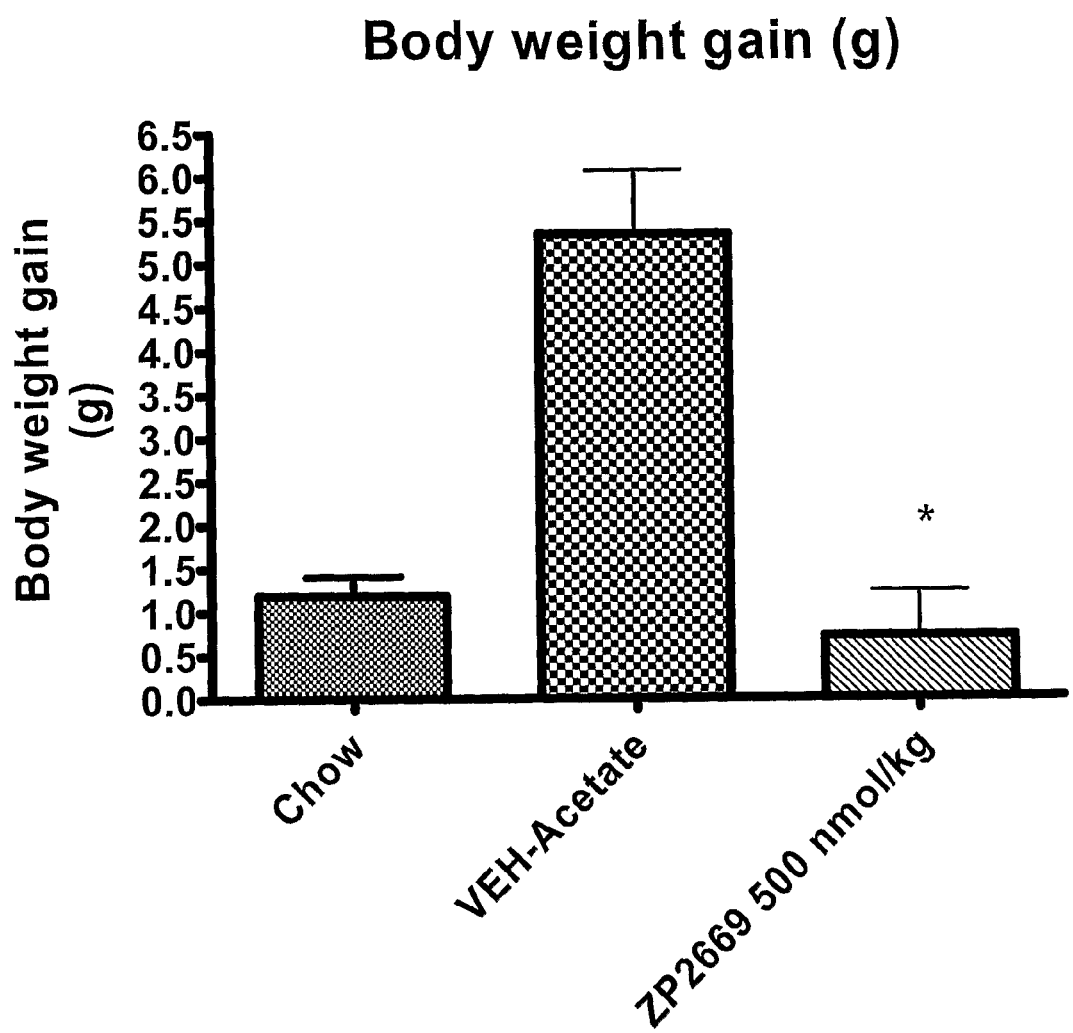
FIG. 3. Effect of 28 day treatment with ZP2669 on body weight in diet induced obese (DIO) mice. C57Bl/6 male mice were put on high fat diet (HFD) and treated (b.i.d.; s.c.) with ZP2669 (500 nmol/kg) or vehicle. A non-obese control group maintained on regular chow was treated with vehicle (CHOW) in the same treatment regimen as the DIO groups. Body weights were recorded daily and used to administer the body weight-corrected doses of peptide throughout the study. ZP2669 decreased body weight gain to a level similar to that observed with chow feeding.

Effect of Subcutaneous Administration on Body Weight Gain in Diet Induced Obese Mice ZP2669 (SEQ ID NO: 4) decreased body weight gain to a level similar to that observed with chow feeding (FIG. 3). The body weight gain was statistically significantly (P<0.05) less than the vehicle group.

Example 7

Effects on LDL and HDL

Exendin-4 is a very potent GLP-1R agonist, but has no effect on the GluR and has no effect in the rat adipocyte lipolysis assay described above. Furthermore, Exendin-4 has no effect on blood concentrations of total cholesterol, HDL, LDL or HDL/LDL ratios (FIGS. 4, 5)

Figure 4:
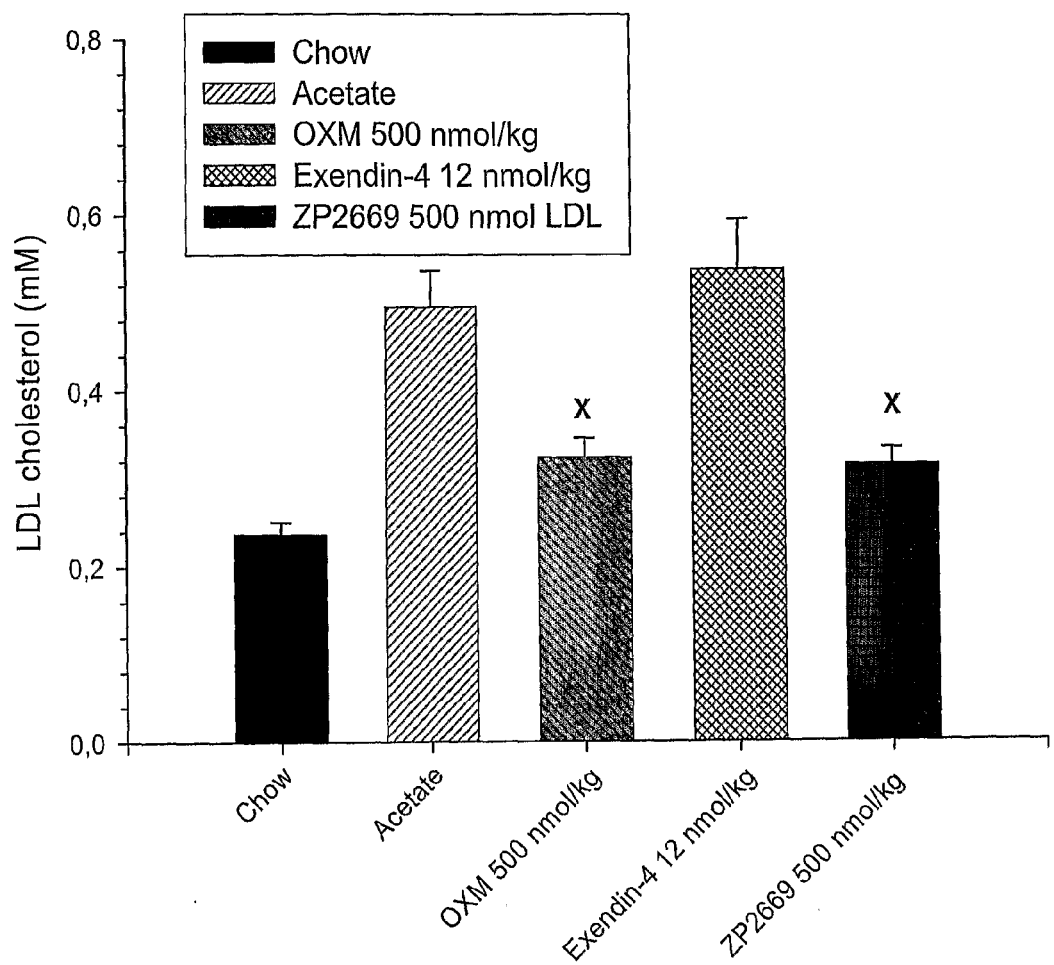
FIG. 4. Effect of dual GluGLP-1 agonist treatment of DIO mice for 4 weeks (b.i.d.) on concentrations of LDL cholesterol. The effect of OXM (p=0.002) and ZP2669 (p=0.0006) were significant compared to vehicle.
Figure 5:
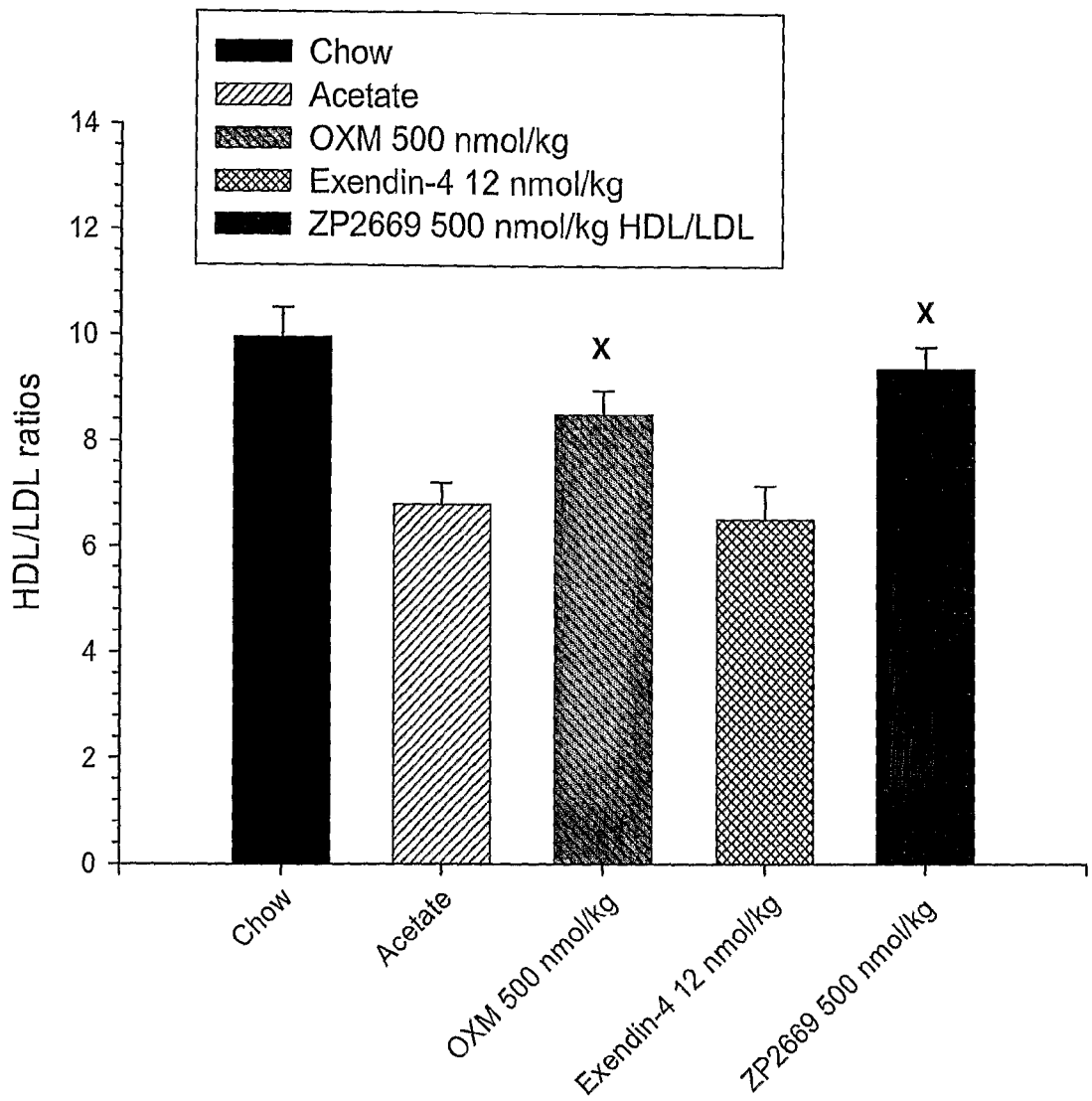
FIG. 5. Effect of dual GluGLP-1 agonist treatment of DIO mice for 4 weeks (b.i.d.) on HDL/LDL ratios. PBS (pH 7.4) was the vehicle used for OXM, exendin-4 while acetate (pH 5.0) was the vehicle used for ZP2669. The effect of OXM (P=0.2%) and ZP2669 (P=0.05%) were significant compared to vehicle.

In contrast, treatment of DIO mice with ZP2669 (SEQ ID NO: 4) had a significant effect on blood concentration of LDL cholesterol (P=0.0006) as well as HDL/LDL ratios (P=0.0005) compared to vehicle (FIGS. 4, 5).

The invention claimed is:

1. A compound having the formula $R^1$-X-Z-$R^2$
wherein
$R^1$ is H, $C_{1-4}$ alkyl, acetyl, formyl, benzoyl or trifluoroacetyl;
$R^2$ is OH or $NH_2$;
X is a peptide which has the formula I:

(SEQ ID NO: 4)
His-Ser-Gln-Gly-Thr-Phe-Thr-Ser-Asp-Tyr-Ser-Lys-

Tyr-Leu-Asp-Ser-Lys-Ala-Ala-His-Asp-Phe-Val-Glu-

Trp-Leu-Leu-Arg-Ala or differs from formula I at up to 4 of the following positions whereby, if different from formula I:
the residue at position 2 is selected from: Aib, D-Ser;
the residue at position 16 is Lys;
the residue at position 17 is selected from: Arg, Leu;
the residue at position 18 is Arg;
the residue at position 20 is selected from: Gln, Lys, Arg;
the residue at position 24 is selected from: Gln, Lys, Arg;
the residue at position 27 is selected from: Met, Lys;
the residue at position 28 is selected from: Asn, Leu; and
the residue at position 29 is Thr;
and Z is absent or a peptide sequence of 1-20 amino acid units selected from the group consisting of Ala, Leu, Ser, Thr, Tyr, Cys, Glu, Lys, Arg, Dbu, Dpr and Orn;
or a pharmaceutically acceptable salt thereof.

2. A compound having the formula $R^1$-X-Z-$R^2$
wherein
$R^1$ is H, $C_{1-4}$ alkyl, acetyl, formyl, benzoyl or trifluoroacetyl;
$R^2$ is OH or $NH_2$;
X is a peptide which has the formula I:

(SEQ ID NO: 4)
His-Ser-Gln-Gly-Thr-Phe-Thr-Ser-Asp-Tyr-Ser-Lys-

Tyr-Leu-Asp-Ser-Lys-Ala-Ala-His-Asp-Phe-Val-Glu-

Trp-Leu-Leu-Arg-Ala or differs from formula I at up to 5 of the following positions whereby, if different from formula I:
the residue at position 2 is selected from: Aib, D-Ser;
the residue at position 16 is Lys;
the residue at position 17 is selected from: Arg, Leu;
the residue at position 20 is selected from: Gln, Lys, Arg;
the residue at position 24 is selected from: Gln, Lys, Arg;
the residue at position 27 is selected from: Met, Lys;
the residue at position 28 is selected from: Asn, Leu; and
the residue at position 29 is Thr;
and Z is absent or a peptide sequence of 1-20 amino acid units selected from the group consisting of Ala, Leu, Ser, Thr, Tyr, Cys, Glu, Lys, Arg, Dbu, Dpr and Orn;
or a pharmaceutically acceptable salt thereof.

3. A compound according to claim 1 wherein X differs from formula I at up to 4 of the following positions whereby, if different from formula I:
the residue at position 2 is selected from: Aib, D-Ser;
the residue at position 16 is Lys;
the residue at position 24 is selected from: Gln, Lys, Arg;
the residue at position 27 is selected from: Met, Lys;
the residue at position 28 is selected from: Asn, Leu; and
the residue at position 29 is Thr.

4. A compound according to claim 1 wherein X comprises one or more of the following groups of residues:
(a) 17-Lys, 18-Ala;
(b) 17-Leu, 18-Ala;
(c) 17-Lys, 18-Ala, 20-His;
(d) 17-Leu, 18-Ala, 20-His;
(e) 17-Lys, 18-Ala, 24-Glu;
(f) 17-Leu, 18-Ala, 24-Glu;
(g) 17-Lys, 18-Ala, 27-Leu;
(h) 17-Leu, 18-Ala, 27-Leu;
(i) 17-Lys, 18-Ala, 29-Ala;
(j) 17-Leu, 18-Ala, 29-Ala;
(k) 17-Lys, 18-Ala, 27-Leu, 29-Ala;
(l) 17-Leu, 18-Ala, 27-Leu, 29-Ala;
(m) 17-Lys, 18-Ala, 27-Leu, 28-Arg, 29-Ala;
(n) 17-Leu, 18-Ala, 27-Leu, 28-Arg, 29-Ala;
(o) 24-Glu, 28-Arg;
(p) 24-Glu, 28-Arg, 27-Leu;
(q) 24-Glu, 28-Arg, 27-Leu, 29-Ala;
(r) 27-Leu, 28-Arg, 29-Ala;
(s) 29-Ala;
(t) 20-Arg, 24-Arg, 27-Lys, 28-Leu;
(u) 17-Arg;
(v) 18-Arg;
(w) 20-Gln;
(x) 24-Gln;
(y) 27-Met, 28-Asn, 29-Thr; or
(z) 24-Lys.

5. A compound according to claim 2 wherein X comprises one of the following groups of residues:
(a) 20-Gln, 24-Gln, 27-Met, 28-Asn, 29-Thr; or
(b) 17-Leu, 20-Gln, 24-Gln, 28-Asn, 29-Thr.

6. A compound according to claim 1 wherein X has the sequence:

H-DSer-QGTFTSDYSKYLDSKAAHDFVEWLLRA; (SEQ ID NO: 6)

H-Aib-QGTFTSDYSKYLDSKAAHDFVEWLLRA; (SEQ ID NO: 7)

HSQGTFTSDYSKYLDSKAARDFVRWLKLA; (SEQ ID NO: 5)

HSQGTFTSDYSKYLDSRAAHDFVEWLLRA; (SEQ ID NO: 12)

HSQGTFTSDYSKYLDSKRAHDFVEWLLRA; (SEQ ID NO: 13)

HSQGTFTSDYSKYLDSKAAQDFVEWLLRA; (SEQ ID NO: 8)

HSQGTFTSDYSKYLDSKAAHDFVQWLLRA; (SEQ ID NO: 9)

HSQGTFTSDYSKYLDSKAAHDFVEWLMNT; (SEQ ID NO: 10)

HSQGTFTSDYSKYLDSKAAHDFVKWLLRA; (SEQ ID NO: 11)

HSQGTFTSDYSKYLDSKAAKDFVEWLLRA; (SEQ ID NO: 18)

HSQGTFTSDYSKYLDKKAAHDFVEWLLRA; (SEQ ID NO: 19)
or

HSQGTFTSDYSKYLDSKAAHDFVEWLLRA. (SEQ ID NO: 20)

7. A compound according to claim 2 wherein X has the sequence:

HSQGTFTSDYSKYLDSKAAQDFVQWLMNT (SEQ ID NO: 15)
or

HSQGTFTSDYSKYLDSLAAQDFVQWLLNT. (SEQ ID NO: 14)

8. A compound according to claim 1 wherein $R^1$ is H.

9. A compound according to claim 1 wherein $R^2$ is $NH_2$.

10. A compound according to claim 1 wherein Z has no more than 25% sequence identity with the corresponding portion of the IP-1 sequence of human oxyntomodulin having the sequence Lys-Arg-Asn-Arg-Asn-Asn-Ile-Ala.

11. A compound according to claim 1 wherein Z has a Cys as the C-terminal residue.

12. A compound according to claim 1 wherein Z is absent.

13. A compound according to claim 1 wherein one or more of the amino acid side chains in the compound is conjugated to a lipophilic substituent or a polymeric moiety.

14. A nucleic acid encoding a compound according to claim 1.

15. An expression vector comprising a nucleic acid according to claim 14.

16. A host cell comprising a nucleic acid according to claim 15 or an expression vector according to claim 15.

17. A pharmaceutical composition comprising a compound according to claim 1, in admixture with a pharmaceutically acceptable carrier.

18. A method of reducing weight gain, promoting weight loss, or for treatment of a condition, said condition being morbid obesity, obesity linked inflammation, obesity linked gallbladder disease and obesity induced sleep apnea, or for treatment of insulin resistance, glucose intolerance, type 2 diabetes, said method comprising administering a therapeutically effective amount of a compound according to claim 1.

19. A compound according to claim 13, wherein one or more of the amino acid side chains in peptide X is conjugated to said lipophilic substituent or polymeric moiety.

20. A compound according to claim 19 wherein X has the sequence:

HSQGTFTSDYSKYLDSK*AAHDFVEWLLRA (SEQ ID NO: 17)

wherein K* indicates a lysine side chain conjugated to isoGlu(Palm).

21. A pharmaceutical composition comprising a nucleic acid according to claim 14, in admixture with a pharmaceutically acceptable carrier.

22. A pharmaceutical composition comprising an expression vector according to claim 15, in admixture with a pharmaceutically acceptable carrier.

23. A pharmaceutical composition comprising a host cell according to claim 16, in admixture with a pharmaceutically acceptable carrier.

24. The compound of claim 1, wherein X has the sequence:

H-DSer-QGTFTSDYSKYLDSKAAHDFVEWLLRA. (SEQ ID NO: 6)

25. The compound of claim 1, wherein X has the sequence:

H-Aib-QGTFTSDYSKYLDSKAAHDFVEWLLRA. (SEQ ID NO: 7)

26. The compound of claim 1, wherein X has the sequence:

HSQGTFTSDYSKYLDSKAARDFVRWLKLA. (SEQ ID NO: 5)

27. The compound of claim 1, wherein X has the sequence:

HSQGTFTSDYSKYLDSRAAHDFVEWLLRA. (SEQ ID NO: 12)

28. The compound of claim 1, wherein X has the sequence:

HSQGTFTSDYSKYLDSKRAHDFVEWLLRA. (SEQ ID NO: 13)

29. The compound of claim 1, wherein X has the sequence:

HSQGTFTSDYSKYLDSKAAQDFVEWLLRA. (SEQ ID NO: 8)

30. The compound of claim 1, wherein X has the sequence:

HSQGTFTSDYSKYLDSKAAHDFVQWLLRA. (SEQ ID NO: 9)

31. The compound of claim 1, wherein X has the sequence:

HSQGTFTSDYSKYLDSKAAHDFVEWLMNT. (SEQ ID NO: 10)

32. The compound of claim 1, wherein X has the sequence:

```
                         (SEQ ID NO: 11)
HSQGTFTSDYSKYLDSKAAHDFVKWLLRA.
```

33. The compound of claim 1, wherein X has the sequence:

```
                         (SEQ ID NO: 18)
HSQGTFTSDYSKYLDSKAAKDFVEWLLRA.
```

34. The compound of claim 1, wherein X has the sequence:

```
                         (SEQ ID NO: 19)
HSQGTFTSDYSKYLDKKAAHDFVEWLLRA.
```

35. The compound of claim 1, wherein X has the sequence:

```
                         (SEQ ID NO: 20)
HSQGTFTSDYSKYLDSKAAHDFVEWLLRA.
```

36. The compound of claim 2, wherein X has the sequence:

```
                         (SEQ ID NO: 15)
HSQGTFTSDYSKYLDSKAAQDFVQWLMNT.
```

37. The compound of claim 1, wherein X has the sequence:

```
                         (SEQ ID NO: 14)
HSQGTFTSDYSKYLDSLAAQDFVQWLLNT.
```

\* \* \* \* \*

UNITED STATES PATENT AND TRADEMARK OFFICE
CERTIFICATE OF CORRECTION

PATENT NO. : 8,685,919 B2  Page 1 of 1
APPLICATION NO. : 13/139493
DATED : April 1, 2014
INVENTOR(S) : Eddi Meier et al.

It is certified that error appears in the above-identified patent and that said Letters Patent is hereby corrected as shown below:

In the claims

Column 37, Line 61, replace "15 or an expression" with --14 or an expression--.

Signed and Sealed this
Twenty-fourth Day of November, 2015

Michelle K. Lee
*Director of the United States Patent and Trademark Office*